(12) United States Patent
Pasula et al.

(10) Patent No.: US 7,258,658 B2
(45) Date of Patent: Aug. 21, 2007

(54) METHOD AND APPARATUS FOR STIMULATING CELLULAR REGENERATION IN A PATIENT

(75) Inventors: Mark Pasula, Palm Beach Gardens, FL (US); Kazimierz Piotrowicz, Chrzanow (PL)

(73) Assignee: Dynamic Research LLC, Palm Beach, FL (US)

( * ) Notice: Subject to any disclaimer, the term of this patent is extended or adjusted under 35 U.S.C. 154(b) by 791 days.

(21) Appl. No.: 10/159,264

(22) Filed: May 29, 2002

(65) Prior Publication Data

US 2005/0124846 A1    Jun. 9, 2005

(30) Foreign Application Priority Data

May 29, 2001    (PL)    ...................................... 347807

(51) Int. Cl.
    *A61N 2/00*    (2006.01)
(52) U.S. Cl. .......................................................... 600/9
(58) Field of Classification Search ............... 600/9–15
    See application file for complete search history.

(56) References Cited

U.S. PATENT DOCUMENTS

| | | | |
|---|---|---|---|
| 4,428,366 A | 1/1984 | Findl et al. |
| 5,160,591 A | 11/1992 | Liboff et al. |
| 5,269,746 A | 12/1993 | Jacobson |
| 6,234,953 B1 | 5/2001 | Thomas et al. |

*Primary Examiner*—John P. Lacyk
(74) *Attorney, Agent, or Firm*—Cohen Pontani Lieberman & Pavane LLP

(57) ABSTRACT

Method and apparatus for treating a patient, including maintaining the patient in a low-frequency, low-intensity magnetic field for an extended period. The frequency of the magnetic field is preferably in the range of from about 40 Hz to about 80 Hz. The intensity of the magnetic field is less than about 2 mT. The patient may preferably use a thermoregulator to select a temperature for treatment, preferably between the temperatures of 65° F. and 100° F. This temperature should be maintained at a uniform temperature over his body, and at a constant temperature over time. The thermoregulator controls heating elements to heat the patient if the patient's body temperature is too low, and controls cooling apparatus, such as fans, air conditioning, or cooling coils, for cooling his patient if the body temperature is too high.

46 Claims, 3 Drawing Sheets

METHOD AND APPARATUS FOR STIMULATING CELLULAR REGENERATION IN A PATIENT

BACKGROUND OF THE INVENTION

1. Field of the Invention

This invention is directed to methods and apparatus for treating patients and, more particularly, to a bed useful for treating patients by facilitating the body's own healing processes to stimulate cellular regeneration and thereby speed up healing of ailments suffered by the patients.

2. Description of the Related Art

When injured, or ill, the human body tends to work to repair itself. In many cases, "bed rest" is all that is required to cure minor aches, pains and illnesses, from a twisted ankle to the flu. Even more serious illnesses may respond to sustained periods of rest and recuperation. The body's own recuperative powers are not always enough for more serious injuries, however, or fast enough for some purposes. For example, football players (professional and amateur) take a tremendous pounding one day (game day) each week, and lesser poundings on practice days. There would be a tremendous benefit in performance if the healing for normal wear, for football players, could be accelerated.

It would also benefit non-athletes as well, if they could accelerate their body's own healing powers and thereby shorten any recovery period for recuperation from illnesses, trauma or any other infirmity. It would be especially useful to find ways to improve the body's own healing functions without use of invasive techniques, such as surgery, drugs, herbs or other remedies.

The difficulty lies in the fact that the body's own restorative processes are not yet completely understood, which has led to the exploration of so-called non-traditional cures, such as holistic medicine, herbal treatments, acupuncture, etc. No such treatment, however, has yet been demonstrated to stimulate true cellular level regeneration, and speed recovery to any great extent.

The inventors have discovered that low-level (in the range of no more than about 2 milli-Teslas: <2 mT and preferably as low as 10 micro-Teslas: <10 µT, or lower) magnetic fields work to stimulate cellular regeneration, and that this regeneration is enhanced when the body is kept at a regulated and constant temperature.

Preliminary research indicates that such treatment is found to provide beneficial effects in speeding recuperation for bruises, strains, and the like, encountered by athletes, and may also assist in recuperation from other illnesses, for example, from bedsores, to nerve damage, to almost any illness afflicting the human body.

There have been prior attempts to utilize alternating electromagnetic fields to promote healing in the human body.

A device for treating hypothermia with a magnetic field was disclosed in U.S. Pat. No. 4,685,462. This device includes two spiral induction coils coupled with an RF generator through an automatic frequency tuning system comprising capacitors and induction coils. In this device, the coils are placed in a non-conducting cylinder which is an element of its casing. One of the coils is fed from the RF generator by a signal of a frequency tuned to the resonance frequency of the device, another by mutual induction. The device is used at a frequency of 2 MHz to 20 MHz, and is intended only to warm a patient who has been subjected to extreme cold, such as a diver submerged in near freezing water. It does not disclose use of magnetic fields to increase cellular regeneration.

Another device, disclosed in European Patent No. 0217011, for medium and high frequency electromagnetic field treatment, includes a pulse generator, a modulator, an amplifier, a band filter and a current regulation circuit. In this device, generated pulses are modulated by their duration or timing, and are amplified by means of power selectors. The amplified signal is applied to the patient through a filter by means of induction coils or electrodes. A signal from the patient is supplied to the device where a regulation system sets the value of rated current which excites the coils and electrodes.

A device for effecting the local, alternating electric and magnetic field of low frequency is disclosed in Polish patent document No. 171930. This device is provided with sensors of the three components of the terrestrial and local magnetic fields, connected with low-pass filters and a microcontroller at the output of which there is connected a pulse generator with three coils coupled thereto, incorporating an input multiplexer with inputs that are sensors and an output multiplexer. Those sensors are connected in parallel between the input multiplexer and the output multiplexer through low-pass filters. This device is used to determine the parameters of all components of the terrestrial and local magnetic fields and of the parameters of the electric field of the biological organism. It detects and signals the occurrence of cyclotronic resonance for specific ions which affect the biological processes of the organism, but is not itself intended for use in treating patients.

European patent document No. 0995463, describes a method and a device for the generation of an electromagnetic field which affects biological processes in living tissue, especially in the human body, by means of a pulsating magnetic field. An electric signal consisting of many discrete pulses having a frequency of from 1 Hz to 1000 Hz is generated and supplied to a device which then generates an electromagnetic field. Preferably, single pulses are grouped in pulse groups and the duration of each pulse group ranges from 0.25 second to 1.2 second. This device does not disclose the use of long-term exposure to a low-frequency magnetic signal for treating a patient.

The disadvantage of all those known devices is that they apply relatively high magnitude magnetic fields in the intensity range of from 1 mT to 10 mT, or they generate a magnetic field in one direction only. Another disadvantage of known devices is that they affect only a specific selected part of the human body through large values of magnetic induction causing excessively rapid stimulation of metabolic processes, while at the same time affecting healthy organs with unnecessarily strong, and therefore potentially harmful, magnetic fields.

Exposure of the human body to strong magnetic fields for extended periods of time is known to cause cellular damage, and so high-intensity magnetic field generating devices are not suitable for use over long periods, such as convalescence from serious long-term illnesses or injuries.

SUMMARY OF THE INVENTION

It is therefore an object of the invention to provide an improved method and device for improving cellular regeneration in a patient by exposing the patient to a low-frequency, low-intensity magnetic field for extended periods.

It is a further object of the invention to provide an improved method and device for treating patients in which cellular regeneration is enhanced by maintaining the body heat of the patient at a substantially constant level during exposure to the low-frequency, low-intensity magnetic field.

The invention is a method and apparatus for stimulating cellular regeneration in a body of a patient, including an electromagnetic field generator for generating a low-frequency, low-intensity magnetic field, and a support for maintaining the body of the patient in the magnetic field during treatment. The frequency of the magnetic field is preferably in the range of from about 40 Hz to about 80 Hz. The intensity of the magnetic field is less than about 2 mT, preferably less than 20 µT, and most preferably less than 10 µT. In addition, because it is preferred that the body of the patient be maintained at a constant temperature, a thermoregulator may be provided to maintain the patient's body at a constant selected temperature for treatment. The thermoregulator controls heating elements to heat the patient if the patient's body temperature is too low, and controls cooling apparatus, such as fans, air conditioning, or cooling coils in the support, for cooling the patient if the body temperature is too high.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, wherein like reference numerals delineate similar elements throughout the several views.

DETAILED DESCRIPTION OF THE PRESENTLY PREFERRED EMBODIMENTS

It is commonly known that electromagnetic fields having a frequency of from about 50 Hz to about 60 Hz and having a strength of about 4.0 kA/m, which corresponds to magnetic induction of approximately 5 mT, is not very good for human health. According to Polish safety regulations, a safe zone where humans may stay without time restraints is considered an area where the strength of a magnetic field of frequency 50 Hz is less than 0.4 kA/m, which corresponds to a magnetic induction of approximately 0.5 mT (500 µT). It is also known that when humans are exposed to magnetic fields less than about 70 µT, the magnetic field affects, through electromotive reactions, the mechanisms of physicochemical reactions of high selectivity by a respective broad-band lowering of the energy of cellular activation. In particular, the body's metabolic processes are stimulated in membrane areas.

We have discovered that, surprisingly, long-term exposure to low-intensity magnetic fields, having a low frequency, in the range of from about 50 Hz to about 60 Hz, lead to the stimulation of metabolic processes in mammals, including humans.

Figure 1:
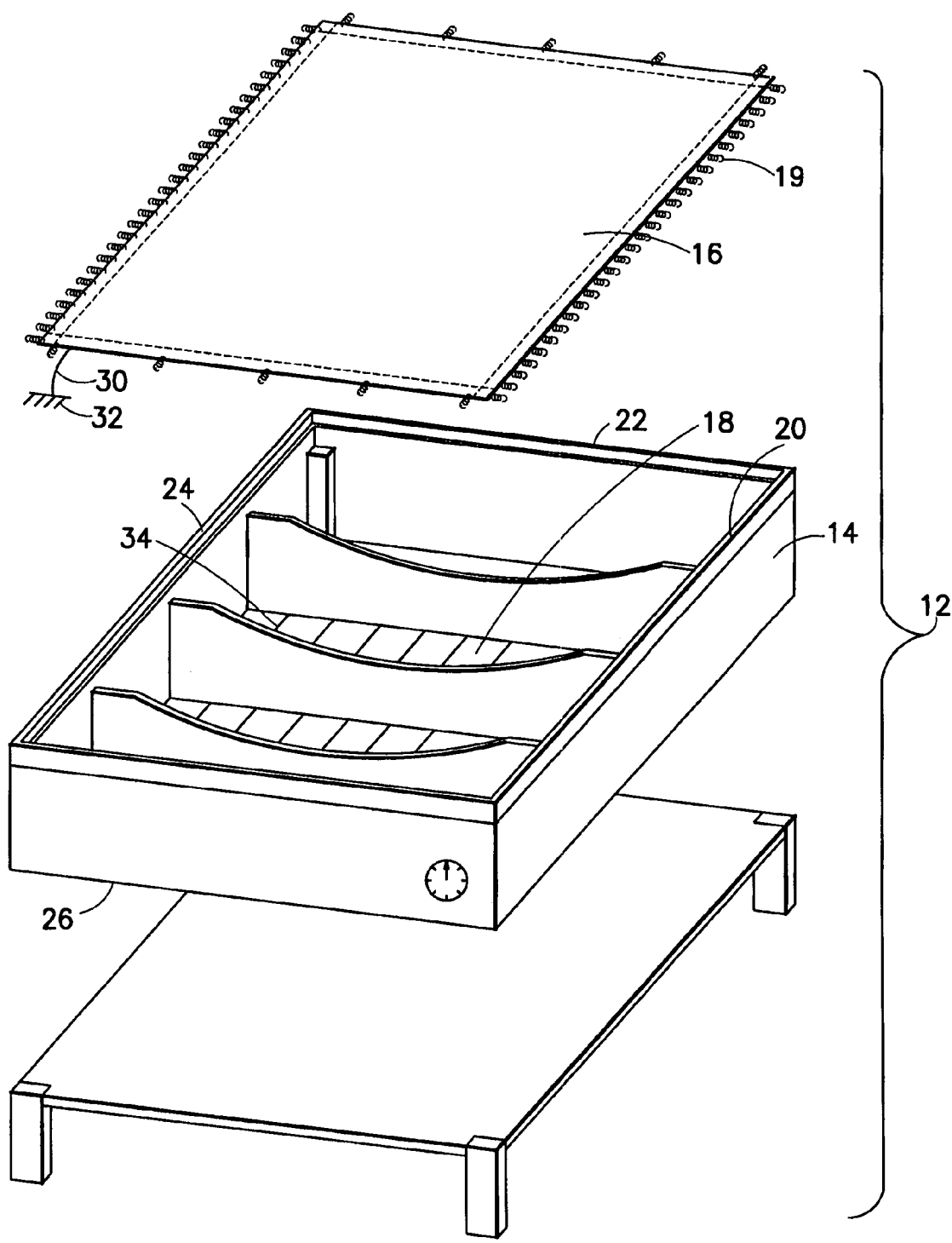
FIG. 1 shows a device in accordance with the invention, shown in exploded perspective.
Figure 2:
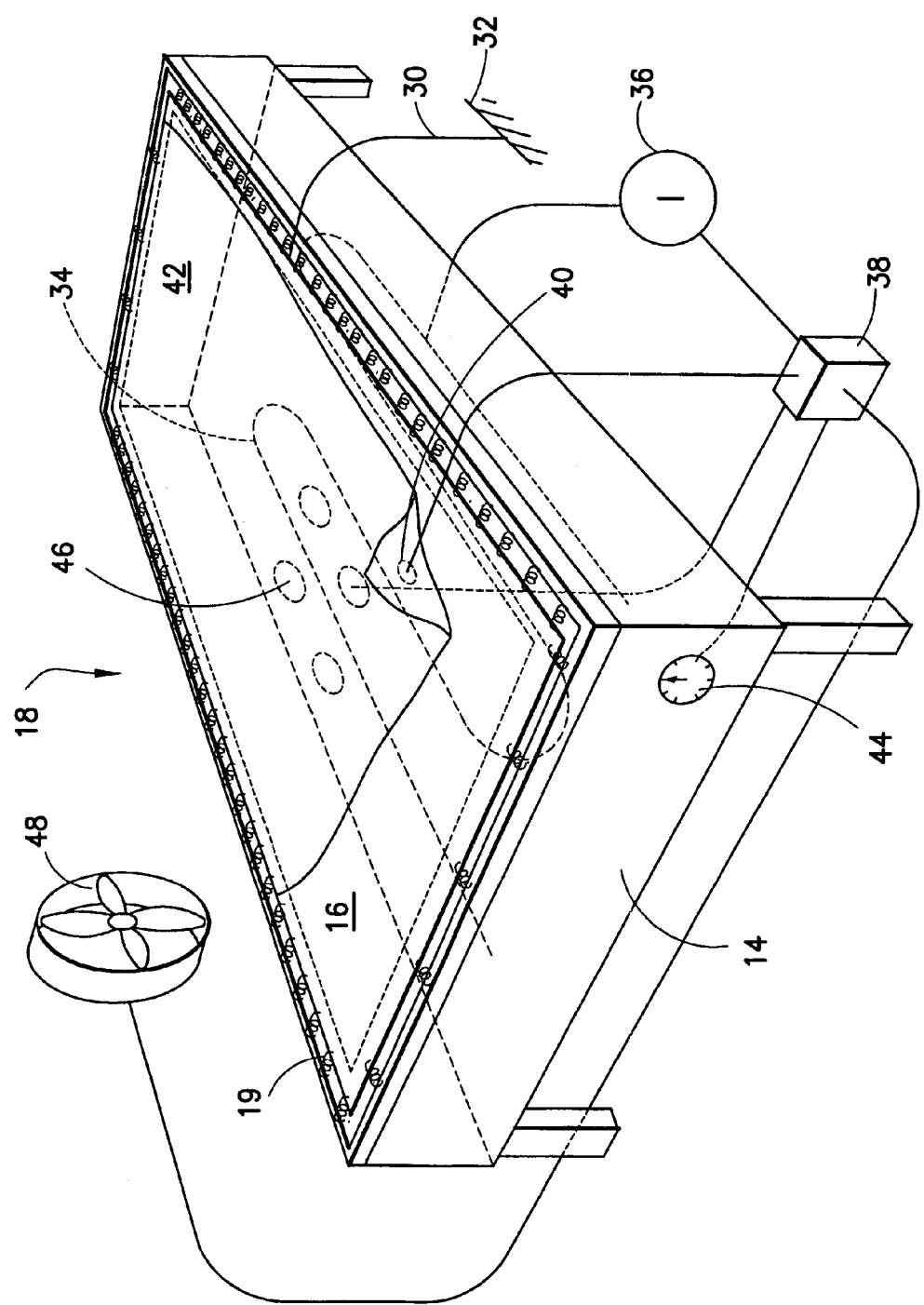
FIG. 2 shows the device of FIG. 1 in the context of a system employing the inventive method.

To facilitate the treatment of humans, or any other mammals with the use of low-frequency, low-intensity magnetic fields, we have constructed a system such as shown in FIGS. 1 and 2, which includes a bed 12, having a tight, preferably rectangular frame 14 which supports a resilient patient supporting surface 16. A means 18 for generating a magnetic field is disposed below supporting surface 16, so that the patient is disposed in the magnetic field generated by magnetic field generator 18, but preferably not in direct contact with generator 18. Often, portions of generator 18 may be hot, and so for the safety and comfort of the patient, direct contact therewith should be avoided.

Supporting surface 16 may be detachable and of any sort providing comfortable support to the patient, such as a conventional mattress, a thin fabric sheet which is preferably air permeable and suspended from frame 14 as by springs 19, or a specially adapted mattress in which the magnetic coils are disposed.

Figure 3:
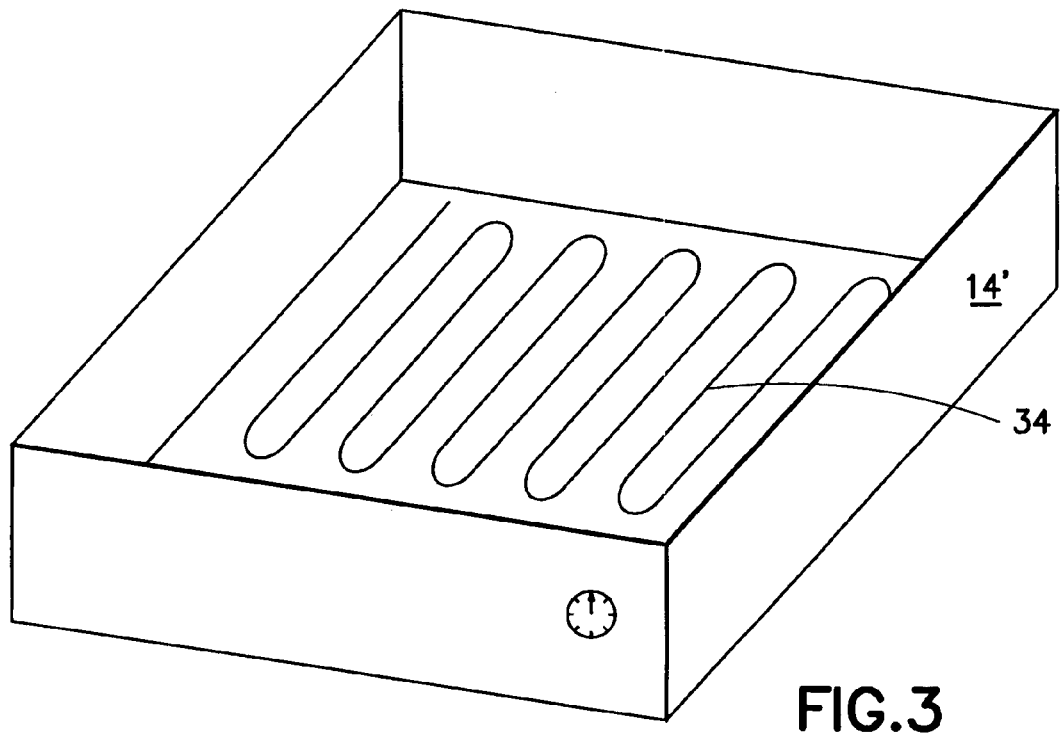
FIG. 3 shows a perspective of an alternate embodiment of the frame of a device in accordance with the invention.

It is also possible supporting surface 16 may be eliminated and frame 14 is made to be water tight. Frame 14 is then filled with a fluid, such as water, as shown in FIG. 3, and the patient is partially immersed and suspended in the water, to avoid contact with a solid surface.

Figure 4:
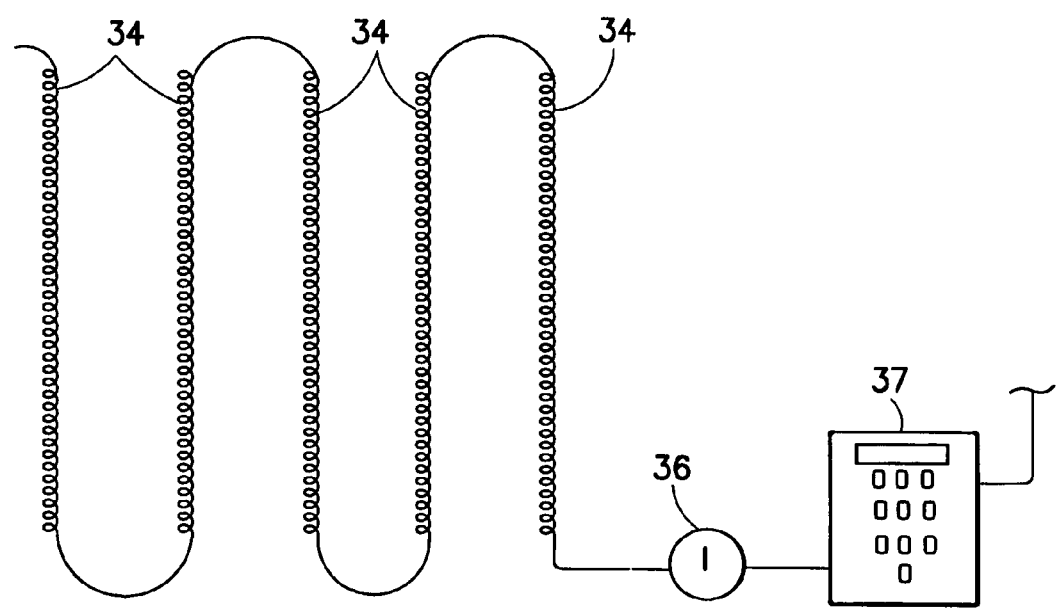
FIG. 4 shows a planar view of a coil used to generate a magnetic field in the devices of FIGS. 1–3.

Frame 14 is preferably open at the top, and has four sides, 20, 22, 24 and 26. Sides 20, 22, 24 and 26 and supporting surface 16 are preferably lined with an insulating material to minimized heat loss. It is preferred that supporting surface 16 has a thin metal thread 30, most preferably made of copper, woven into it. Preferably, thread 30 should cover at least ⅔ of the length of the longer side of supporting surface 16 so that when the patient is laying on supporting surface 16, thread 30 is disposed proximate the patient, regardless of patient size. Thread 30 is connected to an electrical ground 32 and is used to carry excess electrostatic charge away from the patient. A set of coils 34 is disposed proximate supporting surface 16 and is selected to produce an electromagnetic field having a frequency in the range of from about 40 Hz to about 80 Hz, and preferably in the range of from about 50 Hz to about 60 Hz. Coils 34 are energized with alternating current of no more than 24 volts from a current source 36 (FIG. 4) in conventional fashion. The strength of the magnetic field is controlled by an adjuster 37 which, in response to input, alters the intensity of the current passing through coils 34 from current source 36. Preferably, coils 34 are arranged generally parallel to one another (except at their longitudinal ends, which are joined by U-shaped portions) proximate the entire support surface 16. Most preferably, coils 34 are placed on or between two fabrics or materials which are thermoconductive, allowing for the dissipation of heat therefrom. According to the preferred embodiment of the invention, the density of the turns of winding of individual coils is selected so that the value of the magnetic induction provided thereby is within the range of from about 1.2 μT to about 10 μT on the edges frame 14, and preferably should not exceed about 2.6 μT in the vicinity of the patient.

Turning to FIG. 2, to maintain the patient's body heat at a substantially constant selectable temperature, it is preferred that system 10 includes a thermoregulator 38, which comprises one or more conventional temperature sensors 40 placed in close proximity to the body of the patient, for example in supporting surface 16, in a cover 42 disposed on top of r supporting surface 16, or on the body of the patient. A temperature selection means 44, such as a dial or digital input, is connected to thermoregulator 38 allow the patient or treating physician to select a comfortable or treating temperature. Preferably, the temperature is selected within the range of from 65° F. to about 100° F. The precise temperature is not believed critical, but it is believed most desirable that the patient be maintained at a substantially uniform temperature over his entire body, with the possible exception of the head, which is generally maintained outside of cover 42, for ease of breathing. This temperature should be substantially constant over time.

Sensors 40 transmit the value of the current body temperature of the patient to thermoregulator 38, which controls the temperature near the patient by switching an air chamber heating/cooling unit 46 on or off. Although four heating/cooling units 46 are shown, fewer or more units may be used. At the same time, coils 34 may be switched on or off to regulate the generation of the magnetic field from generator 18, to control heat generated thereby. It is preferred that the body temperature of the patient be maintained constant with a variance of no more than about 0.4° F. from the selected temperature. If the body temperature rises more than 0.4° F., the patient is cooled by heating/cooling units 46, while if the body temperature falls more than 0.4° F. below the desired temperature, the patient is warmed by heating/cooling units 46.

Heating may conveniently be accomplished by providing heating/cooling elements 46 in either or both of support surface 16 and cover 42, as, for example, by an electric blanket-type mechanism, as is well-known. Alternatively, external heating elements such as convection heaters, space heaters, hot air blowers, and the like may be provided. Cooling may likewise be accomplished in conventional fashion, by providing cooling coils in either or both of support surface 16 and cover 28, or by providing an ambient cooling element 48, such as an air conditioner, fan, ceiling fan or other known mechanism for cooling an environment. The design and construction of these conventional features is a mere matter of design choice, and well within the abilities of those of ordinary skill in the art without undue experimentation.

A patient lying on support surface 16 is subject to the electromagnetic field generated by means 18, with concomitant regulation of temperature in this area, thereby subjecting the patient to natural thermal regulation and intensification of physiological metabolism processes, producing a distinct improvement in his physical condition. Depending upon the desired course of treatment, it is possible for patients to remain in the inventive device for extended periods, without suffering any harmful effects. The invention can be used for long-term hospital patients (in which case the inventive device could be used as a hospital bed), or for patients being treated at home, during their normal sleep cycle (in which case the inventive device could be used as a bed).

Where a patient is being treated for any appreciable period of time, it is presently preferred that the magnetic field be cycled on and off in two hour intervals to maintain the body in a constant state of flux, which is currently believed to be most efficacious in treatment of a patient, but this is not a necessary component of the treatment process. Longer or shorter cycling periods, including a constant "on" condition, may be employed, as desired.

The invention is not limited by the embodiments described above which are presented as examples only but can be modified in various ways within the scope of protection defined by the appended patent claims.

For example, while the above description presupposes that the patient may be human, it should also be possible to treat other animal patients, particularly mammalian patients.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A device for treating a mammal, said mammal having a body with a magnetic field, comprising:
   means for generating a magnetic field having an intensity of no more than about 2 mT;
   means for maintaining said body of said mammal in said magnetic field; and
   means for regulating a body temperature for said mammal.

2. The device of claim 1, wherein said magnetic field has a frequency of from about 40 Hz to about 80 Hz.

3. The device of claim 1, wherein said magnetic field has a maximum intensity of about 20 μT.

4. The device of claim 3, wherein said magnetic field has a maximum intensity of about 10 μT.

5. The device of claim 1, wherein said means for regulating said body temperature of said mammal includes means for uniformly heating said body of said mammal, except for a head of said mammal.

6. The device of claim 5, wherein said means for heating said body of said mammal includes means for maintaining a body heat of said mammal at a predetermined temperature.

7. The device of claim 6, wherein said predetermined temperature is substantially in the range of from about 65° F. to about 100° F.

8. The device of claim 7, further comprising means for selecting said predetermined temperature.

9. The device of claim 1, wherein said means for regulating includes means for cooling said mammal.

10. The device of claim 9, wherein said means for regulating includes means for maintaining a body heat of said mammal at a predetermined temperature.

11. The device of claim 10, wherein said predetermined temperature is substantially in the range of from about 65° F. to about 100° F.

12. The device of claim 11, further comprising means for selecting said predetermined temperature.

13. The device of claim 1, further comprising means for removing electrostatic charge from said mammal present in said device.

14. The device of claim 13, wherein said means for removing electrostatic charge includes a grounded conductive metal wire disposed to contact said mammal when present in said device.

15. The device of claim 14, wherein said wire is comprised of copper.

16. The device of claim 1, wherein said means for maintaining comprises a frame and a surface supported by said frame on which surface said patient may be disposed.

17. The device of claim 16, wherein said frame is thermally insulated.

18. The device of claim 16, wherein said surface comprises a fabric support attached at its periphery to said frame.

19. The device of claim 18, wherein said fabric support includes a wire positioned in said fabric support to remove electrostatic charge from said patient.

20. The device of claim 18, wherein at least a portion of said magnetic field generating means is disposed within said fabric support.

21. The device of claim 1, wherein said magnetic field generating means comprises a plurality of inductive coils.

22. A method for stimulating cellular regeneration in a body of a mammal, comprising:
generating a magnetic field having an intensity of no more than about 2 mT;
maintaining said mammal in said magnetic field for a period of time; and
regulating a body temperature of said mammal
whereby cells of said body of said patient may regenerate during said period of time.

23. The method of claim 22, wherein said magnetic field has a frequency of from about 40 Hz to about 80 Hz.

24. The method of claim 22, wherein said magnetic field has a maximum intensity of about 20 µT.

25. The method of claim 24, wherein said magnetic field has a maximum intensity of about 10 µT.

26. The method of claim 22, wherein said step of regulating said body temperature of said mammal includes heating said body of said mammal uniformly except for a head of said mammal.

27. The method of claim 26, wherein said step of heating said body of said mammal includes maintaining a body heat of said mammal at a predetermined temperature.

28. The method of claim 27, wherein said predetermined temperature is substantially in the range of from about 65° F. to about 100° F.

29. The method of claim 28, further comprising the step of selecting said substantially constant temperature.

30. The method of claim 22, wherein said step of regulating includes cooling said body temperature of said mammal.

31. The method of claim 30, wherein said step of regulating includes maintaining a body heat of said mammal at a predetermined temperature.

32. The method of claim 31, wherein said predetermined temperature is substantially in the range of from about 65° F. to about 100° F.

33. The method of claim 32, further comprising the step of selecting said predetermined temperature.

34. The method of claim 22, further comprising removing undesired electrostatic charge from said mammal.

35. A system for treatment of a mammal, comprising:
a frame defining a treatment area;
a surface substantially disposed in said treatment area, on which said mammal may be supported;
a magnetic field generator for generating a magnetic field in the vicinity of said patient when supported on said surface, said magnetic field having an intensity of no more than about 2 mT, said magnetic field generator including a plurality of coils disposed proximate said surface, so that said mammal is substantially disposed within said magnetic field when supported on said surface;
a cover for retaining body heat of said mammal, said cover being disposed above said surface, so that said mammal may be positioned between said cover and said surface when undergoing treatment; and
a thermoregulator for maintaining said body heat of said mammal at a substantially constant predetermined temperature.

36. The system of claim 35, further comprising a heater responsive to said thermoregulator to heat said mammal when said body heat of said mammal falls below said predetermined temperature.

37. The system of claim 35, further comprising cooling means responsive to said thermoregulator for cooling said mammal when said body heat of said mammal rises above said predetermined temperature.

38. The system of claim 37, wherein said cooling means cools ambient air in the vicinity of said mammal.

39. The system of claim 35, further comprising means for selecting said predetern] med temperature.

40. The system of claim 35, wherein said magnetic field has a frequency of from about 40 Hz to about 80 Hz.

41. The system of claim 35, wherein said low-intensity magnetic field has a maximum intensity of about 20 µT.

42. The system of claim 35, wherein said low-intensity magnetic field has a maximum intensity of about 10 µT.

43. The system of claim 35, wherein said surface comprises an air-permeable fabric.

44. The system of claim 35, wherein said surface includes a fluid.

45. The system of claim 35, wherein said cover includes a thermoconductive fluid.

46. The system of claim 35, further comprising a grounding wire disposed within one of said cover and said surface, for removing electrostatic charge from said mammal when positioned within said treatment area.

* * * * *